US009463236B2

(12) United States Patent
Kido et al.

(10) Patent No.: US 9,463,236 B2
(45) Date of Patent: Oct. 11, 2016

(54) RSV MUCOSAL VACCINE

(75) Inventors: Hiroshi Kido, Tokushima (JP); Dai Mizuno, Tokushima (JP); Hirotsugu Ueda, Tokyo (JP); Koji Yoshikawa, Tokyo (JP); Keisuke Ohsumi, Tokyo (JP); Nobuyuki Yamamoto, Tokyo (JP); Kenji Sudo, Tokyo (JP)

(73) Assignee: TOKUSHIMA UNIVERSITY, Tokushima (JP)

( * ) Notice: Subject to any disclaimer, the term of this patent is extended or adjusted under 35 U.S.C. 154(b) by 87 days.

(21) Appl. No.: 14/241,596

(22) PCT Filed: Aug. 29, 2012

(86) PCT No.: PCT/JP2012/071831
§ 371 (c)(1),
(2), (4) Date: Apr. 22, 2014

(87) PCT Pub. No.: WO2013/031827
PCT Pub. Date: Mar. 7, 2013

(65) Prior Publication Data
US 2015/0297713 A1 Oct. 22, 2015

(30) Foreign Application Priority Data
Aug. 29, 2011 (JP) ................................ 2011-185873

(51) Int. Cl.
*A61K 39/155* (2006.01)
*A61K 39/12* (2006.01)
(Continued)

(52) U.S. Cl.
CPC ............. *A61K 39/155* (2013.01); *A61K 39/12* (2013.01); *A61K 39/39* (2013.01); *C07K 14/001* (2013.01);
(Continued)

(58) Field of Classification Search
CPC .................. C12N 2760/18534; A61K 39/12; A61K 2039/55555; A61K 39/39; A61K 2039/543; A61K 38/00; A61K 2039/541; A61K 2039/544
See application file for complete search history.

(56) References Cited

U.S. PATENT DOCUMENTS

| | | | |
|---|---|---|---|
| 7,220,545 | B2 | 5/2007 | Binz et al. |
| 8,211,442 | B2 | 7/2012 | Kido et al. |

(Continued)

FOREIGN PATENT DOCUMENTS

| | | | |
|---|---|---|---|
| JP | WO 2009/123119 | * 10/2009 | ............ A61K 39/39 |
| WO | 95/27787 | 10/1995 | |
| WO | 2004/083251 | 9/2004 | |
| WO | 2005/097182 | 10/2005 | |
| WO | 2007/018152 | 2/2007 | |
| WO | 2009/123119 | 10/2009 | |

OTHER PUBLICATIONS

Yunus et al. Elevated temperature triggers human respiratory syncytial virus F protein six-helix bundle formation. Virology, 2010; 396: 226-237.*

(Continued)

*Primary Examiner* — Janet L Andres
*Assistant Examiner* — Stuart W Snyder
(74) *Attorney, Agent, or Firm* — Wenderoth, Lind & Ponack, L.L.P.

(57) ABSTRACT

A composition comprising the following composition: an AD vehicle including a synthetic peptide and a lipid, wherein the synthetic peptide includes the amino acid sequence KnLm (wherein n is 4 to 8 and m is 11 to 20), a carboxylvinyl polymer and an RSV antigen. The composition has an antibody producing ability which is further higher than that of a conventional mucosal vaccine, hence capable of exerting excellent anti-virus antigen-specific IgA antibody- and IgG antibody-inducing effect in the nasal wash and the serum, respectively, even with an extremely small quantity of an RSV antigen.

8 Claims, 3 Drawing Sheets

(51) Int. Cl.
*C07K 14/005* (2006.01)
*C07K 14/00* (2006.01)
*A61K 39/39* (2006.01)
*C12N 7/00* (2006.01)
*A61K 39/00* (2006.01)

(52) U.S. Cl.
CPC ............... *C07K 14/005* (2013.01); *C12N 7/00* (2013.01); *A61K 2039/541* (2013.01); *A61K 2039/543* (2013.01); *A61K 2039/55511* (2013.01); *A61K 2039/55516* (2013.01); *A61K 2039/55555* (2013.01); *C12N 2760/00034* (2013.01); *C12N 2760/18522* (2013.01); *C12N 2760/18534* (2013.01); *C12N 2760/18551* (2013.01)

(56) References Cited

U.S. PATENT DOCUMENTS

| | | | |
|---|---|---|---|
| 8,268,321 | B2 | 9/2012 | Kido et al. |
| 8,287,887 | B2* | 10/2012 | Kido et al. ................ 424/278.1 |
| 2006/0251675 | A1 | 11/2006 | Hagen |

OTHER PUBLICATIONS

Low et al., "The RSV F and G glycoproteins interact to form a complex on the surface of infected cells", Biochemical and Biophysical Research Communications, 2008, vol. 366, No. 2, pp. 308-313.

Kim et al., "Respiratory Syncytial Virus Disease in Infants Despite Prior Administration of Antigenic Inactivated Vaccine", American Journal of Epidemiology, 1969, vol. 89, No. 4, pp. 422-434.

Lindell et al., "A Novel Inactivated Intranasal Respiratory Syncytial Virus Vaccine Promotes Viral Clearance without Th2 Associated Vaccine-Enhanced Disease", PLoS one, 2011, vol. 6, No. 7, e21823, pp. 1-14.

Anderson et al., "Prospects for defined epitope vaccines for respiratory syncytial virus", Future Microbiology, 2010, vol. 5, No. 4, pp. 585-602.

Bukreyev et al., "The Secreted G Protein of Human Respiratory Syncytial Virus Antagonizes Antibody-Mediated Restriction of Replication Involving Macrophages and Complement", Journal of Virology, 2012, vol. 86, No. 19, pp. 10880-10884.

* cited by examiner

RSV MUCOSAL VACCINE

TECHNICAL FIELD

The present invention relates to a pharmaceutical composition which induces a mucosal IgA and a blood IgG to an RSV efficiently, typically an RSV mucosal vaccine, preferably an RSV mucosal vaccine for nasal administration.

BACKGROUND

Patent Literatures (PTLs) 1 and 2 made detailed descriptions of the demerits in conventional inactivated vaccines or toxoids, as well as the current states with regard to the development of mucosal vaccines and immunoadjuvants.

As described in PTLs 1 and 2, the requirement of switching from a conventional vaccine of being inoculated subcutaneously or intramuscularly to a mucosal vaccine inducing the production of an IgA antibody on mucosa which is a natural viral infection route, is widely and profoundly recognized. Especially as a next generation vaccine in the 21st century, a mucosal vaccine inducing IgA antibody production, topical immunity or mucosal immunity is desired to be developed and brought into practical use all over the world, but it has not be achieved yet.

In response to these problems, the present inventions have invented an, antigen-drug (AD) vehicle, which is a complex of a pulmonary surfactant protein B and/or a pulmonary surfactant protein C and a lipid(s), and a mucosal vaccine consisting of this AD vehicle and an antigen (PTL 1). The present inventors also found that by adjusting the weight ratio V/A of the AD vehicle amount (V) to the antigen amount (A), the selective production of an IgA antibody and the production of both IgA and IgG antibodies are convertible, and then developed a mucosal vaccine based on such action mechanism (PTL 2). PTLs 1 and 2 also disclose the effectiveness of fragments (peptides) of the pulmonary surfactant proteins B and C.

In addition, as a result of a study on various variants of pulmonary surfactant protein fragments for their antibody production enhancing effects, the present inventors have invented an AD vehicle [hereinafter abbreviated as AD vehicle (a)] comprising as a component a synthetic peptide KnLm (wherein n is 4 to 8 and m is 11 to 20) which, in spite that it is a smaller-sized peptide than the partial peptides disclosed in PTLs 1 and 2, has a potent antibody production-inducing or -enhancing effect, especially for an exclusive production of a secretory IgA antibody as well as an excellent and effective inductory effect on the production of both secretory IgA and blood IgG, and a mucosal vaccine consisting of this AD vehicle (a) and an antigen (PTL 3).

While the inventions of PTLs 1 to 3 relate to a mucosal vaccine having broad utility, the effectiveness was confirmed by using an influenza virus.

On the other hand, the mucosal vaccine has been investigated for respiratory disease-causing viruses other than the influenza virus. Among such viruses, an RSV is a major virus causative of a common cold syndrome, and is one of the viruses the immune for which is difficult to acquire because its infection occurs many times in a life.

The RSV infection causes bronchiolitis and pneumonia in infants, elders and immunodeficiency patients, and especially about 30% of primary RSV infection cases in infants lead to lower airway inflammation. Among such cases, 1 to 3% progress to a severe state requiring hospitalization, because of which a vaccine therefor is highly demanded.

The RSV is an RNA virus belonging to Paramyxoviridae, and can roughly be grouped into subtype A and subtype B. It is known that, on the surface of the virus, there are F protein important for fusion with a host cell (Non Patent Literature (NPL) 1), G protein involved in adhesion to a host cell (NPL1), and SH protein, Accordingly, a whole viral particle or these proteins have been studied as antigens for many RSV vaccines.

In a usual method, the first option for a vaccine against a virus is a formalin-inactivated vaccine. Since such a method exhibited a sufficient vaccine effect against the influenza virus, formalin-inactivated vaccines have been employed for a long time.

While the formalin-inactivated vaccine was tested in 1960's also against the RSV, it resulted not only in the lack of the vaccine effect on the RSV but also in serious side effects in infants, unlike the cases against the influenza virus (NPL2).

Thereafter, the RSV vaccine was subjected to researching for split vaccines which are a mixture of a part of the virus constituents and an adjuvant (PTL 4, PTL 5). Until today, attempts to develop the RSV vaccines involved an attempt to specify the antigen having an infection preventing ability, a development of an effective adjuvant and a development of vaccine inoculation methods. Previous reports include a report of infection-preventing antibody induction by a novel inactivation method (NPL3), a report that the RSV membrane fusion F protein is effective as an antigen (NPL4) and a report that the RSV G protein is effective as an antigen (NPL5). In the current state, the results may differ depending on the method for administrating an RSV antigen as a vaccine and on the combination of the adjuvant to be added with the antigen. Nonetheless, there is no RSV vaccines approved on marketed yet, because of their insufficient vaccine effect or side effects.

CITATION LIST

Patent Literature

PTL 1: WO 2005/097182
PTL 2: WO 2007/018152
PTL 3: WO 2009/123119
PTL 4: WO2004/083251
PTL 5: WO1995/027787

Non Patent Literature

NPL 1: Biochem. Biophys. Res. Commun. 366 (2), 308-313 (2008)
NPL 2: Am J Epidemiol. 1969 April;89 (4):422-34,
NPL 3: PLoS one. 6(7), e21823, 1-14 (2011)
NPL 4: Future Microbiol. 5, 585-602 (2010))
NPL 5: J. Virol. Doi:10.1128/JVI.01162-12 (2012))

SUMMARY

Technical Problem

Since most of the RSV vaccines which have been previously or currently subjected to clinical development are percutaneously injectable vaccines, they can induce an IgG in blood but can not induce an IgA antibody which plays an important role in preventing viral infection on a mucosa.

On the other hand, PTL 5 discloses a nasal RSV vaccine utilizing an attenuated cholera toxin as an adjuvant which can induce an IgA in a nasal mucosa. However, nasal vaccines employing bacterial toxins pose a concern of a facial paralysis as a side effect (The New England Journal of Medicine 2004; 350:896-903). Accordingly, an alternative adjuvant is required for a safe nasal vaccine.

Another problem associated with a conventional mucosal vaccine is a poor production efficiency due to the requirement of a larger amount of the antigen when compared with a percutaneously injectable vaccine.

An object of the present invention is to provide an RSV vaccine which has an IgG inducing effect equivalent to that of a conventional percutaneously injectable vaccine while allowing an IgA expected to have an RSV infection preventing effect to be induced in a nasal cavity and which does not pose a concern of a side effect such as facial paralysis, thereby exerting a safe and excellent RSV infection preventing effect.

An object of the present invention is to provide an improved RSV mucosal vaccine having an antibody producing ability which is further higher than that of the mucosal vaccine in the case of applying the AD vehicle (a) described in PTL 3 to an RSV antigen, and hence having an ability of exerting an excellent infection suppressing effect on blood and mucosa via nasal administration of the antigen in an amount which is as small as that of the percutaneously injectable vaccine.

Solution to Problem

The present inventors identified that a carboxyvinyl polymer (hereinafter abbreviated as CVP) which is a gelling agent employed in the influenza virus antigen-containing nasal drops and mucosally applicable vaccine, as a means for further enhancing the mucosal vaccine antibody induction when applying the AD vehicle (a) described in PTL 3 to the RSV antigen, acts on the AD vehicle to increase the quantity of the antigen carried to antigen presenting cells, thereby being effective in inducing the mucosal IgA and blood IgG, thus establishing the present invention.

Accordingly, the present invention is a composition comprising the following composition:
(a) an AD vehicle [hereinafter abbreviated as AD vehicle (a)] consisting of a synthetic peptide and a lipid(s), wherein the synthetic peptide consisting of the amino acid sequence KnLm (wherein n is 4 to 8 and m is 11 to 20);
(b) a carboxylvinyl polymer; and,
(c) an RSV antigen. In particular, the present invention is a pharmaceutical composition, is preferably a mucosal vaccine and more preferably a mucosal vaccine for a transnasal administration.

In the composition of the invention, the RSV antigen (c) is in an amount, even in combination with the AD vehicle (a) or in combination with the carboxyvinyl polymer (b), incapable of producing an antigen-specific mucosal IgA and blood IgG sufficient for exerting an effective immune induction and an infection-preventing effect.

In one aspect of this mucosal vaccine, the synthetic peptide is a peptide consisting of the amino acid sequence of SEQ ID NO: 1 or 2, and preferably a peptide consisting of the amino acid sequence of SEQ ID NO: 1.

In another aspect of this mucosal vaccine, the lipid is at least one of phosphatidyl choline, dipalmitoylphosphatidyl choline, phosphatidyl serine, phosphatidyl glycerol, phosphatidyl inositol, phosphatidyl ethanolamine, phosphatidic acid, lauric acid, myristic acid, palmitic acid, stearic acid and oleic acid. More specifically, the lipids are a mixture of dipalmitoylphosphatidyl choline, phosphatidyl glycerol and palmitic acid.

The RSV antigen in this composition is a whole RSV particle, an attenuated strain's whole RSV particle, splits from the whole particle, F protein, G protein, SH protein, N protein, P protein, M2-1 protein, M2-2 protein, L protein, M protein, NS1 protein, or NS2 protein or combinations thereof, or, the whole RSV particle as a mixture containing such proteins, with an RSV-F protein being especially preferred.

Those also included are these proteins modified in a gene engineering manner such as introduction of a variation, deletion, insertion of a partial sequence, and substitution, as well as partial sequences of each protein and chimera with different proteins. Preferably, an F protein which has been modified in a gene engineering manner or a chimera containing at least a part of the F protein is employed.

The method for producing a composition using the RSV-F protein as an antigen is conducted preferably by subjecting a mixture of the RSV-F protein and the AD vehicle to lyophilization or ultrasonic treatment followed by mixing with a carboxyvinyl polymer.

As used herein, "mucosal IgA and blood IgG sufficient for exerting an effective immune induction" is the IgA, and the IgG the quantities of which serve to suppress the viral proliferation in an RSV cell infection system.

In the following description, a composition consisting of a synthetic peptide and lipids may be referred to as an "AD vehicle (a)", and a mucosal vaccine consisting of the AD vehicle (a) and an RSV antigen may be referred to as a "RSV+AD vehicle", and a mucosal vaccine consisting of an RSV antigen and a CVP may be to "RSV+CVP". The composition of the present invention consisting of the AD vehicle(a), CVP and RSV antigen may be referred to as a "RSV+ADF vehicle+CVP". In addition, the composition of the present invention may be referred to as a "RSV mucosal vaccine" or a RSV mucosal vaccine "RSV+AD vehicle+CVP".

Advantageous Effects of Invention

The inventive RSV mucosal vaccine, "RSV+AD vehicle+CVP", has an extremely potent RSV antigen-specific IgA and IgG antibody inducing effect and an induced antibody-associated viral proliferation suppressing effect in an RSV cell infection system. Such effects are so extremely marked that they cannot be predicted from the effect of "RSV+AD vehicle" which applies the mucosal vaccine in PTL. 3 to an RSV antigen and from the effect of "RSV+CVP" which applies CVP in US Patent publication U.S. Pat. No. 5,158,761 to the RSV antigen.

As shown for example in Experiment Example 1, "RSV+AD vehicle" does not exhibit a sufficient antibody production induction, while the inventive RSV mucosal vaccine "RSV+AD vehicle+CVP" exhibits an IgA production level higher by 24.3 times and an IgG production level higher by 12.1 times in terms of antibody titer when compared with "RSV+AD vehicle". In addition, the inventive RSV+AD vehicle+CVP exhibits an IgA production level higher by 21.1 times and an IgG production level higher by 4.6 times in terms of antibody titer when compared with RSV+CVP.

Due to such a potent antibody inducing ability, an infection-preventing effect which can not be obtained using a conventional mucosal vaccine is achieved.

The AD vehicle (a) and the CVP themselves, contained in the inventive mucosal vaccine "RSV+AD vehicle+CVP", have been proven to have no antigen recognizing cell-stimulating effect. Accordingly, it is extremely unlikely, upon administering the inventive mucosal vaccine "RSV+

AD vehicle+CVP", that unexpected side effects by any antigen other than the RSV antigen, such as autoimmune disease and post-vaccination allergy exacerbation, may occur.

DESCRIPTION OF EMBODIMENTS

The RSV mucosal vaccine "RSV+AD vehicle+CVP" of the invention consists of the following composition.
Synthetic Peptide
A synthetic peptide consists of the amino acid sequence of KnLm (wherein n is 4 to 8, and m is 11 to 20). KnLm has n×K(Lys) residues on the N-terminus side and m×L residues on the C-terminus side. Such a synthetic peptide may be any of the following peptides. In the parenthesis, the abbreviation of a peptide is indicated. The amino acid residue is indicated as a single letter code.

```
SEQ ID NO: 1(K6L16): KKKKKKLLLLLLLLLLLLLLLL

SEQ ID NO: 2(K6L11): KKKKKKLLLLLLLLLLL
```

SEQ ID NO: 1 (K6L16) consists of 6 K(Lys) residues on the N-terminus side and 16 L residues on the C-terminus side, and SEQ ID NO: 2 (K6L11) consists of 6 K(Lys) residues on the N-terminus side and 11 L residues on the C-terminus side. These synthetic peptides should be those prepared according to known chemical synthesis methods whose purities are 95% or higher, Lipid
A phospholipid contained in a pulmonary surfactant, such as phosphatidyl choline, dipalmitoylphosphatidyl choline, phosphatidyl serine and phosphatidyl glycerol is employed preferably. Otherwise, phosphatidyl inositol, phosphatidyl ethanolamine, phosphatidic acid, sphingomyelin, and the like may also be employed. As fatty acids, lauric acid, myristic acid, palmitic acid, stearic acid, palmitooleic acid, oleic acid, and the like may be employed. It is also possible to employ a lipid derived from aquatic animals such as whale and dolphin whose lungs are inflated dynamically.
Carboxyvinyl Polymer (CVP)
The CVP is a hydrophilic polymer obtained by polymerizing acrylic acid as a main component, and commercially available ones such as Hivis Wako 103, Hivis Wako 104, Hivis Wako 105, Sigma Corporation's product pAA130 (Sigma, St. Louis, Mo., Cat No. 181293), pAA450 (Sigma, Cat No. 181285) and pAA1250 (Sigma, Cat No. 306215) can be employed. Among these, Hivis Wako 104, and Sigma Corporation's products pAA130 and pAA1250 which are employed widely in producing cosmetic and pharmaceutical gels are preferred. After producing a 0.2 to 2.0% by weight solution of CVP in pure water or physiological saline under ultrasonic treatment, a NaOH neutralizing solution can be employed to adjust to pH5.0 to 10.5, while it is preferred to employ a pH by which the stability of the vaccine antigen is not affected adversely. For example, an influenza split vaccine antigen is adjusted to pH6.8 to 8.0, preferably pH7.0 to 7.2
Antigens
The RSV antigen may be a whole particle, attenuated strain's whole particle (International Publication WO2010/053883 (Wyeth, attenuated strain)), splits from the whole particle, F protein (Proc. Natl. Acad. Sci. U.S.A. 81 (24), 7683-7687 (1984) (A2 strain F protein)), G protein (Proc. Natl. Acad. Sci. U.S.A. 82 (12), 4075-4079 (1985) (A2 strain G protein)), SH protein (Virology 141 (2), 283-291 (1985) (A2 strain SH protein)), N protein (Virology 146 (1), 69-77 (1985) (A2 strain N protein)), P protein (J. Virol. 52 (3), 991-994 (1984) (A2 strain P protein)), M2-1 protein, M2-2 protein (J. Virol. 55 (1), 101-110 (1985) (A2 strain M2-1, M2-2 protein)), L protein (Virology 183 (1), 273-287 (1991) (A2 strain L protein)), M protein (J. Virol. 50 (1), 92-99 (1984) (A2 strain M protein)), NS1 protein, or NS2 protein (Virology 143 (2), 442-451 (1985) (A2 strain NS1 protein, NS2 protein)), or combinations thereof, or, the whole RSV particle as a mixture containing such proteins. The RSV-F protein is especially preferred.

Those also exemplified are these proteins modified in a gene engineering manner such as introduction of a variation, deletion, insertion of a partial sequence, and substitution, (International Publication WO2010/077717 (application including Novavax #683), International Publication WO2009/079796 (ID Bio Medical, Pre Form immobilized-modified F), International Publication WO2010/075491 (Rochester University, F antigen self-folding neutralization antibody epitope), International Publication WO2010/149745 (GSK, trimer promoting modified F protein), International Publication WO2010/039224 (Massachusetts Medical University, RSV-modified protein and VLP), International Publication WO2010/059689 (LYGOCYTE, F protein VLP), International Publication WO2009/000433 (PEVION virosome), United States Publication US2010/111989 (PEVION—modified F protein), United States Publication US2008/0003236 (United States Department of Health and Human Services, GENVEC vector+RSV), International Publication WO2010/057650 (Bavarian Nordic, Vaccinia vector+RSV-F), International Publication WO2008/110627 (Pierre Fabre Medicament, RSV microcapsule), Vaccine 28 (34), 5543-5550 (2010) (Groningen University, Virosome), Vaccine 20 (29-30), 3436-3442 (2002) (Siena University, Virosome), Vaccine 27 (46), 6415-6419 (2009) (EPFL, Virosome), Vaccine 25, 7132-7144 (2007) (Alphavax, RSV-F protein+replicon).

In addition, those which may also be exemplified include, but are not limited to, partial sequences of each protein (aforementioned PTL 9, United States Publication US2010/0172925 (NHRI, CTL epitope), International Publication WO2011/017442 (United States Department of Health and Human Services, G protein peptide antigen), International Publication WO2011/050168 (United States Department of Health and Human Services, neutralizing antibody epitope fragment)), and chimeras of each protein with a different protein (JP3290662 (Connote laboratories Ltd., PIV & RSV chimera), Published Japanese translation No. 2010-522540 (ID Bio Medical, FGF chimera), International Publication WO2011/046925 (TECHNO VAX, F & M1 & M2 protein VLP), International Publication WO2010/149743 (GSK, RSV+PIV3+MPV chimera)). A chimera of the F protein and another protein is employed preferably.

It is also possible that these antigens may be derived from the subtypes other than the RSV subtype A, such as RSV subtype B (Proc. Natl. Acad. Sci. U.S.A. 94 (25), 13961-13966 (1997) (B1 strain total protein, cs mutant, genome sequence AF013254), (B9320 strain total protein, genome sequence AY353550)). In still another aspect, the antigen may be derived from a virus belonging to Pneumovirus subfamily (International Publication WO2010149743 (GSK, RSV+PIV3+MPV chimera)).

While these antigens are not subjected to any particular quantitative limitation, each may be prepared and used in such an amount that, when used alone, or especially used in combination with the AD vehicle (a) or in combination with the carboxyvinyl polymer (CVP), does not produce of the antigen specific mucosal IgA and blood IgG sufficient for exerting an effective immune induction.

The followings are the description of a method for preparing an AD-vehicle (a) and an RSV mucosal vaccine (RSV+AD vehicle+CVP) of the invention from the materials described above.

AD Vehicle (a) Preparation

Several lipids from those listed above are mixed in a suitable ratio and suspended in a chloroform:methanol (2:1 (v/v)) mixture for example at a concentration as a lipid of 10 mg/mL, and employed as a lipid component. The synthetic peptide is dissolved in ethanol for example at a concentration of 5.0 mg/mL. Then these lipid component and synthetic peptide are mixed. The mixing ratio involves about 0.2 to about 12.0% by dry weight for the synthetic peptide, and about 88 to about 99.8% by dry weight for the lipid. This mixture is evaporated into dryness at about 40° C. using a rotary evaporator and resuspended in 10% ethanol at a suitable concentration, stirred and mixed for about 15 minutes in a water bath at about 45° C. to yield a uniform dispersion, which is then freezed and dried. This dried substance is stored at about −30° C., and at every time of use it is suspended with pure water or physiological saline, and then subjected to an ultrasonic wave, a homogenizer, a mixer, a stirrer and the like, to form a uniform dispersion.

RSV Mucosal Vaccine "RSV+AD Vehicle+PCV" Preparation

The aforementioned AD vehicle (a), CVP and RSV antigen are mixed in a suitable ratio. Thus, in the case of an RSV vaccine, the AD vehicle solution is admixed in the vaccine stock solution so that the ratio of the AD vehicle amount (V) to the antigenic protein (A) on the dry weight basis, i.e. V/A, becomes a desired value. The dry weight of the antigenic protein (A) to be administered to a single mouse is about 0.01 to about 100 µg/kg body weight, preferably about 0.03 to about 50.0 µg/kg body weight.

In such an antigen amount, the V/A for inducing the IgA antibody production predominantly and selectively is preferably about 0.1 to about 1.0. On the other hand, the V/A for inducing the production of both of the IgA and IgG antibodies is about 1.0 to about 100, preferably about 5 to about 20. In the V/A described above, about 60% or more of the antigen is bound to the AD vehicle, and the resultant RSV mucosal vaccine is capable of inducing the IgA antibody production and/or the IgG antibody production efficiently.

The CVP concentration of the final nasal vaccine solution to which CVP was added is about 0.1% to 1.0%, preferably 0.3% to 0.8%. The AD vehicle (a), the antigen and CVP can be mixed uniformly using a homogenizer, a mixer, an agitator, a stirrer and the like.

While the suitable production method, for the purpose of allowing the RSV mucosal vaccine to cause an effective antibody induction, may vary depending on the type of the antigen employed, the production method involving an ultrasonic treatment step and the production method involving a lyophilization step as described below are recommended when using an F protein (Experiment 1) which is preferred especially as an RSV antigen.

In the method including ultrasonic treatment, as shown in Example 1 described below, the RSV-F antigen and the AD vehicle are mixed, and then subjected to an ultrasonic treatment for 3 minutes, and finally combined with an equal volume of a 1% CVP solution in physiological saline, thereby producing the RSV mucosal vaccine (RSV+AD vehicle+CVP). This method is identical to the method described in PTL 3 except for using RSV antigen instead to HA and adding CVP.

On the other hand, the method including a freeze-dry process comprises, as exemplified in Example 2, the following steps:

(1) suspending the AD vehicle and the antigenic protein in water (pure water);
(2) repeating warming and stirring once or more;
(3) freezing and lyophilizing,
(4) suspending the lyophilized samples in physiological saline to adjust to a predetermined concentration; and,
(5) adding the CVP solution dissolved in physiological saline.

As described in Experiment 1 below, this is an excellent method serving to enable a enhanced production of the antigen-specific IgA and IgG, as same as the aforementioned production method including ultrasonic treatment.

The RSV mucosal vaccine "RSV+AD vehicle+PCV" thus prepared may be used in a single dosing, but it is used preferably in two dosings (initial immunization and secondary immunization) or three dosings (initial immunization, secondary immunization and tertiary immunization). Such a repeated immunizing treatment allows the antibody titres of antigen-specific IgA and IgG to be increased markedly. The two or three vaccine dosings are conducted at intervals of 1 week to 3 weeks, preferably about 2 weeks. The administration of the RSV mucosal vaccine "RSV+AD vehicle+PCV" of the invention can be done to the nasal cavity as well as the oral cavity or the vaginal cavity (see for example Lubrizol Pharmaceutical Bulletin, Polymers for Pharmaceutical Applications, Lubrizol Advanced Materials, Inc. 2008).

The present invention is further detailed typically in the following Examples but the invention is not limited to the following examples.

EXAMPLE 1

[A Manufacture of RSV Mucosal Vaccine Involving Ultrasonic Treatment]

An AD (a) vehicle was prepared as described below. Dipalmitoylphosphatidylcholine (DPPC), phosphatidyl glycerol (PG) and palmitic acid (PA) were mixed in a ratio of 75:25:10 (w/w/w) and suspended in a chloroform:methanol (2:1 (v/v)) mixture solution at a concentration as a phospholipid of 10 mg/ml to obtain a lipid component. A synthetic peptide K6L16 (KKKKKKLLLLL-LLLLLLLLLLL: SEQ ID NO: 1) (product of GenScript Inc.) having a purity of 95% or higher was dissolved in methanol at 5.0 mg/mL. The lipid component (DPPC:PG:PA=75:25:10, w/w/w) solution and the K6L16 peptide solution were mixed in a weight ratio of the phospholipid component:K6L16=100:2 and evaporated into dryness at 40° C. using a rotary evaporator. This was resuspended in 10% ethanol at a concentration as a phospholipid of 4 mg/ml, stirred and mixed for about 15 minutes in a water bath at about 45° C. to yield a uniform dispersion. This was freezed and dried, and then stored as an AD vehicle at −30° C.

Then, the aforementioned AD vehicle (a) was employed to prepare an RSV mucosal vaccine "RSV+AD vehicle+CVP" as described below.

The lyophilized AD vehicle (a) was used after being suspended just before use in a physiological saline. The RSV-F protein prepared by the following method was used as an antigen. A DNA including the base sequence of SEQ ID NO:3 was expressed in a silkworm larva-Baculovirus expression system (formerly Katakura Industries Co., Ltd., currently Sysmex Corporation), Purification using an anti-FLAG antibody affinity gel (Sigma-Aldrich Co. LLC.) obtained an RSV-F protein including the amino acid sequence of SEQ ID NO:4. The protein concentration of the antigen solution measured by DC Protein Assay (Bio-Rad Laboratories Inc.) was 2.03 mg/mL.

The RSV-F antigen and the AD vehicle were mixed in such a ratio that the ratio of the antigen solution protein amount (A) to the AD vehicle (a) solution phospholipid amount (V), i.e. VA=8, subjected to an ultrasonic treatment involving On and OFF three times repetitively at intervals of 30 seconds to accomplish the ultrasonic treatment for 3 minutes in total including ON for 90 seconds and OFF for 90 seconds in total (Handy sonic model UR-20P, TOMY SEIKO Co., LTD), then dissolved in physiological saline, and then combined with a neutralized 1% CVP (Hivis Wako 104) at a final concentration of 0.5%. Thus, the composition contained in 4 μl in total to be administered into the both nasal cavities of a single mouse with 2 μl being given to each nostril is the RSV antigenic protein amount/AD vehicle solution's phospholipid amount/CVP weight=1.0 μg/8.0 μg/20 μg.

Hereinafter the RSV mucosal vaccine "RSV+AD vehicle+CVP" produced by the method including the ultrasonic treatment will be designated as "RSV+SF-10". While the SF-10 amount is AD vehicle (8.0 μg)+CVP (20 μg)=28 μg as described above, the following description employs the designation SF-10 (8.0 μg) to represent the amount of the AD vehicle (a) phospholipid which serves as a basis for the vehicle effect of the adjuvant. The SF-10 amounts in other Examples are indicated as values excluding the CVP amounts.

EXAMPLE 2

[Example of RSV Mucosal Vaccine Production Involving Lyophilization Step]

To the RSV-F protein solution similar to that in Example 1, a lyophilized AD vehicle (a) powder dissolved in pure water was admixed. The resultant suspension was warmed at 42° C. for 10 minutes in a water bath, and after 3 and 7 minutes of the warming the suspension was homogenized by stirring for 10 seconds. After the warming, the suspension was frozen overnight at −20° C. to −75° C., and then lyophilized to obtain a dried powder. The lyophilized powder was stored at 4° C. to −30° C. Just before use, the lyophilized powder was dissolved in a 0.5% CVP solution prepared in advance in a physiological saline with stirring gently while avoiding foaming to obtain an RSV mucosal vaccine "RSV+AD vehicle+CVP". The quantity of the RSV antigen protein contained in 4 μL of the vaccine in total to be given to both nostrils, each of which was to receive 2 μL per single mouse, was 1.0 μg, and the phospholipid content of the AD vehicle (a) was 8.0 μg. Hereinafter the RSV mucosal vaccine "RSV+AD vehicle+CVP" produced by this method involving the lyophilization step is designated as RSV+SF-10F.

COMPARATIVE EXAMPLE 1

The mucosal vaccine (RSV+AD vehicle (a)) was prepared. The RSV-F protein and the AD vehicle (a) were identical to those in Example 1, and the preparation of the vaccine was conducted as same to Example 1, to which the equal volume of saline was added as substitute for 1% CVP (Hivis Wako 104) at a final concentration of 0.5%. The RSV-F antigenic protein amount was 1.0 μg and the AD vehicle (a) amount was 8.0 μg.

COMPARATIVE EXAMPLE 2

The mucosal vaccine (RSV+CVP) was prepared. The RSV-F protein was diluted with pure water, and the equal volume of 1% CVP (Hivis Wako 104) was added. The RSV-F antigenic protein amount was 1.0 μg, the AD vehicle (a) amount was 8.0 μg, and the final concentration of CVP was 0.5%.

COMPARATIVE EXAMPLE 3

RSV-protein was diluted with a saline and used as a vaccine. Administration amount of RSV-F protein per one mouse was 1.0 μg.

COMPARATIVE EXAMPLE 4

SF-10 was prepared by adding 1% CVP (Hivis Wako 104) at a final concentration of 0.5% to 5.0 μg of AD vehicle (a).
Experiment 1
Using mice, the antibody production enhancing effects of the nasal mucosal vaccines with AD vehicle (a) and various RSV antigens were tested.
1. Mucosal Vaccine Four types of virus antigens shown in Table 1, namely, RSV ether split, RSV-F protein (secretory), RSV-G protein (secretory), RSV-G protein's partial epitope sequence (Gen- Bank/CAA51765, amino acid sequence 156-175) each conjugated with ovalbumin (OVA), bovine serum albumin (BSA), or influenza hemagglutinin (HA) were mixed with the AD vehicle in the ratio shown in Table 1, with the nasally inoculated antigen quantity per mouse being designated as low dose (L) or high dose (H), to prepare the RSV mucosal vaccines by the lyophilization method described in Example 2, and thereafter the final preparation was made by the method of Comparative Example 1 and the mice were inoculated nasally.

TABLE 1

| | Type of Antigen | Vaccine/Adv | Dose per mouse (Low: L, High: H) |
|---|---|---|---|
| 1 | RSV ether split | 8.2 | 0.24, 0.97 |
| 2 | F protein (-transmembrane domain) secreted form Baculovirus-silkworm expression system | 2.0 | 1.01, 4.06 |
| 3 | G protein epitope peptide (G-pep) | 30.8 | 0.06, 0.26 |
| | G-pep-OVA | 4.3 | 0.47, 1.88 |
| | G-pep-BSA | 4.0 | 0.50, 1.98 |
| | G-pep-HA | 4.7 | 0.43, 1.72 |
| 4 | G protein (-transmembrane domain) secreted form Baculovirus-silkworm expression system | 2.2 | 0.90, 3.60 |

2. Animals

Female BALB/c mice (6-8 week-old) purchased from Japan Charles River Lob were used. All animal experiments were conducted in Institute for Animal Experimentation, Tsukuba Research Center of Astellas Pharma Inc, in accordance with the guidelines of Committee for Animal Experimentation of Astellas Pharma Inc.

3. Immunization Method

In administering the vaccine nasally, 2 μl of 4 mucosal vaccines described in abave Section 1 was respectively administered to each nostril, thereby instillating 4 μl in total to the both nasal cavities of each mouse under anesthesia with Somnopentyl (Kyoritsu Seiyaku Co.) (81.0 mg/kg). The tests were conducted with Low dose (L) and High dose (H) of antigens. Each group consisted of 10 mice. The amounts of antigen (L and H) were shown in Table 1.

The secondary boost immunization was conducted by the nasal administration of the identical dose of vaccines at two weeks after the initial immunization. After the secondary immunization for two weeks, the tertiary immunization was conducted by a similar method, and at two weeks after last immunization the samples were taken. While the vaccine was given three times in total, the secondary immunization as the final immunization can give almost similar results.

4. Preparation of Mouse Nasal Cavity Washes and Serum

At two weeks after the tertiary immunization, nasal cavity washes and serum were prepared for measurements of the viral RSV antigen-specific IgA and IgG. The procedures were same to the description of a publication (Mizuno D, Ide-Kurihara M, Ichinomiya T, Kubo I, Kido H. Modified pulmonary surfactant is a potent adjuvant that stimulates the mucosal IgA production in response to the influenza virus antigen. J Immunol. 2006; 176:1122-30).

A vaccine-treated mouse was anesthetized with Somnopentyl to a thoracolaparotomy, and an Atom venous catheter 3 Fr having nodes (Atom Medical Corporation, Tokyo, Japan) was inserted via the incised tracheal duct to the direction of the nasal cavity, to which 1 mL of the physiological saline was infused and the fluids coming out of the nose were collected. The fluids were employed as nasal washes. In addition, a blood was taken out from the abdominal aorta or the heart, centrifuged to prepare a serum.

5. Quantification of Anti-RSV Antibody

The anti-RSV-specific IgA and IgG levels in the nasal cavity washes and serum were quantified by ELISA assay.

The ELISA assay was conducted by the method described below. Onto each well of a 96-well Nunc immunoplate (Nalgen Nunc International, NY, USA), 5 ng of the antigen protein identical to the antigen employed for the immunization was layered. Then, 50 μL of 0.05M carbonate-bicarbonate (pH 9.6) was added and an immobilization reaction was conducted at 4° C. overnight. Thereafter, a washing solution (25 mM Tris, 0.15 M NaCl, 0.05% Tween 20) was employed for rinsing three times to remove the antigen solution. To each well, 200 μL of 50 mM Tris-HCl buffer solution (pH 7.6) containing 0.15 M NaCl and 1% BSA was added, and a blocking reaction was conducted for 1 hour at room temperature. After rinsing each well three times with the washing solution, 50 μL of a nasal wash or serum diluted to a suitable level with a sample binding buffer solution (50 mM Tris, 0.15 M NaCl, 1% BSA, 0.05% Tween 20, pH 7.6) was added and reacted for 1 hour at room temperature. Using an anti-mouse IgA peroxidase or an anti-mouse IgG peroxidase (Sigma) as a secondary antibody, a chromogenic reaction was conducted using TMB Microwell Peroxidase Substrate System (Kirkegaard & Perry Laboratories, Inc., MD, USA). The reaction was quenched by adding 50 μL of 2N $H_2SO_4$ (NacalaiTesque, Inc.) to each well, and the absorbance at 450 nm was measured using EnVision.

6. Results

Figure 1:
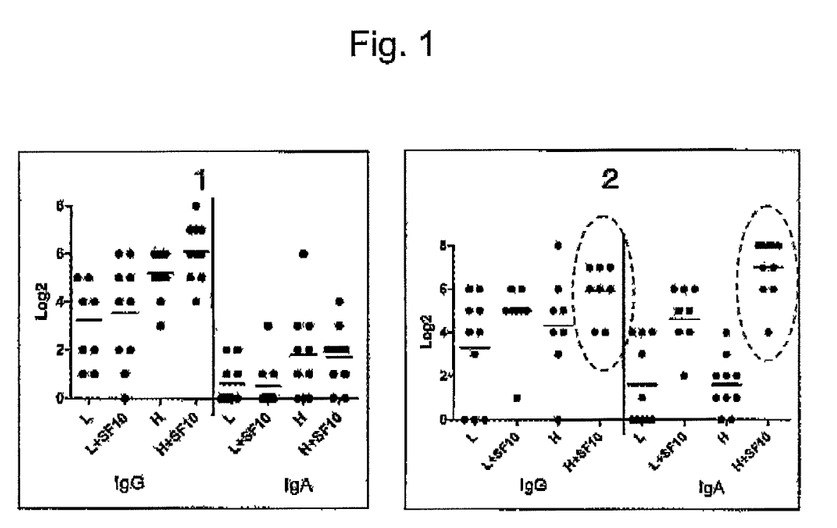
FIG. 1 shows the results of Experiment 1 representing the nasal wash IgA level and the serum IgG level after administering an ether split RSV antigen and F protein as antigens nasally to mice. In the figure, L and H indicate the low dose (L) and the high dose (H) of the antigen protein shown in Table 1, while L+SF-10 and H+SF-10 indicate the respective antigen doses (L and H) combined with the AD vehicle and then subjected to lyophilization and finally supplemented with the aforementioned CVP. The serum anti-RSV IgG antibody titer is indicated on the left, while the nasal wash anti-RSV IgA antibody titer is indicated on the right. The results are obtained from each 10 animals.
Figure 2:
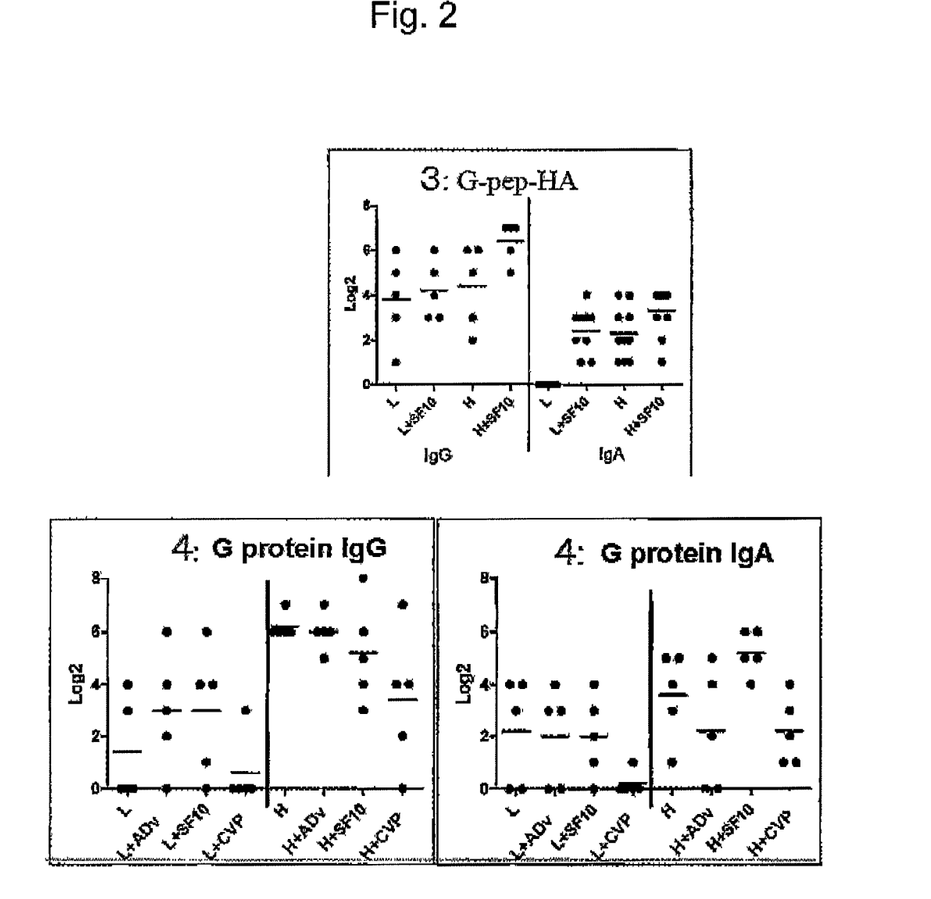
FIG. 2 shows the results of Experiment 1 representing the nasal wash IgA level and the serum IgG level after administering an RSV-G protein or an HA conjugate of an RSV-G protein epitope peptide as antigen nasally to mice, each group consisting of 10 animals. In the figure, L and H indicate the low dose (L) and the high dose (H) of the antigen protein shown in Table 1, while L+SF-10 and H+SF-10 indicate the respective antigen doses (L and H) combined with the AD vehicle and then subjected to lyophilization and finally supplemented with the aforementioned CVP. The serum anti-RSV IgG antibody titer is indicated on the left, while the nasal wash anti-RSV IgA antibody titer is indicated on the right. The upper panel (3) shows an example of the HA conjugate of the antigen epitope amino acid of the RSV-G protein, while the lower panels (4) show the case using the RSV-G protein as an antigen. The experiment system in which the AD vehicle is added to the antigen dose (L and H) is designated as L(H)+ADv, and L(H)+CVP, L(H)+ADv+CVP is designated as L(H)+SF-10.

In FIG. 1, the serum anti-RSV IgG antibody level and the nasal wash anti-RSV IgA antibody level after nasal inoculation of the RSV mucosal vaccine containing the RSV ether split antigen or RSV-F protein antigen as antigen are indicated as log 2 titers. In FIG. 2, the serum anti-RSV IgG antibody level and the nasal wash anti-RSV IgA antibody level after nasal inoculation of the antigen made by conjugating the RSV-G protein antigen or the G-protein antigen epitope peptide to HA are indicated as log 2 titers. The low dose (L) and the high dose (H) of the antigen quantity administered per mouse are as described in Table 1.

While the shift of the antigen quantity from L to H tended to increase the antibody titer for any of the antigens as shown in FIGS. 1 and 2, the RSV-F protein exhibited the most excellent nasal wash anti-RSV IgA antibody production and blood anti-RSV IgG antibody production. The RSV ether split antigen and the RSV-G protein antigen allowed the blood IgG antibody induction to occur, but exhibited a difficulty in allowing the nasal wash anti-RSV IgA antibody production to occur. These results confirmed that the RSV antigen suitable to the SF-10 adjuvant is the F protein.

Experiment 2

The samples listed below were tested for their antibody production enhancing effect. As an RSV antigen, the RSV-F protein was employed.

Physiological saline
RSV alone (Comparative Example 3)
RSV+CVP (Comparative Example 2)
RSV+SF-10F (Example 2)
RSV+AD vehicle (a) (Comparative Example 1)
RSV+SF-10 (Example 1)

1. Animals

The mice similar to those in Experiment 1 were employed.

2. Immunization Method

In nasal vaccination, any of the aforementioned 5 samples was administered at 2 µL per nostril, thus 4 µL in total being instilled to both nostrils of a mouse anesthetized with Somnopentyl (Kyoritsuseiyaku Corporation) (81.0 mg/kg). Each group consisted of 10 mice.

A second boost immunization was conducted by the nasal administration of the identical dose of the vaccines two weeks after the initial immunization. Two weeks after the second immunization, a third immunization was conducted by a similar method, and two weeks after the third immunization specimens were taken. While the vaccines were given three times in total, the second immunization can be the final immunization and give almost similar results.

3. Preparation of Mouse Nasal Cavity Washes and Sera

The conditions similar to those in the method of Experiment 1 were employed.

4. Anti-RSV-F Antibody Titer Measurement

The nasal wash anti-RSV-F-IgA level and the serum anti-RSV-F-IgG level were quantified by an ELISA assay.

The ELISA assay was conducted by the method described below. Onto each well of a 96-well Nunc immunoplate (Nalgen Nunc International, NY, USA), 5 ng of the RSV F protein was immobilized and the measurement was conducted by the method described in Experiment 1.

7. Results 7-1. Antibody Production Enhancing Effect

Figure 3:
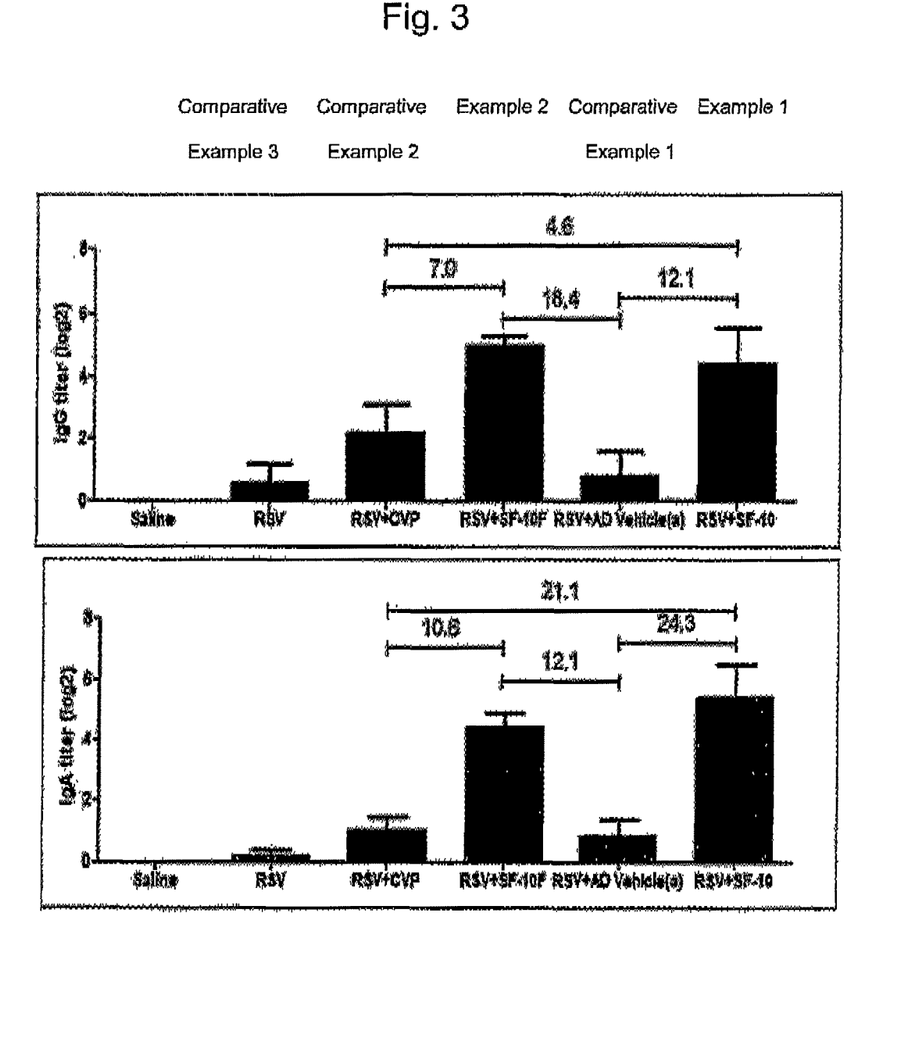
FIG. 3 shows the results of Experiment 2 representing the nasal wash IgA level (bottom) and the serum IgG level (top) when administering each sample nasally to mice.

The results of the induction of the anti-RSV antibodies are shown in the lower panel in FIG. 3 (nasal wash anti-RSV IgA antibody) and in the upper panel in FIG. 3 (blood anti-RSV IgG antibody). The results can be summarized as follows.

(1) The RSV+SF-10 (Example 1) treatment group exhibited, when compared with the group of the RSV+AD vehicle (a) (Comparative Example 1), a level of the IgA which was higher by 24.3 times and a level of the IgG which was higher by 12.1 times in terms of antibody titer.

(2) The RSV+SF-10 (Example 1) treatment group exhibited, when compared with the group of the RSV+CVP (Comparative Example 2), a level of the IgA which was higher by 21.1 times and a level of the IgG which was higher by 4.6 times in terms of antibody titer.

(3) The RSV+SF-10F (Example 2) treatment group exhibited, when compared with the group of the RSV+AD vehicle (a) (Comparative Example 1), a level of the IgA which was higher by 12.1 times and a level of the IgG which was higher by 18.4 times in terms of antibody titer.

(4) The RSV+SF-10F (Example 2) treatment group exhibited, when compared with the group of the RSV+CVP (Comparative Example 2), a level of the IgA which was higher by 10.6 times and a level of the IgG which was higher by 7.0 times in terms of antibody titer.

(5) The RSV antigen alone (Comparative Example 3) exhibited an antibody titer which was extremely low.

Such a markedly excellent antibody inducing effect of RSV+SF-10 and RSV+SF-10F was not observed when employing the RSV antigen alone, and far exceeded the range predicted from an application of a simple combination of the AD vehicle (a) known in PTL 3 with CVP known in U.S. Pat. No. 5,158,761 to the RSV antigen. It was also revealed that, for the production of a composition including a combination of the SF-10 with the RSV F protein, both of lyophilization and ultrasonic treatment can be employed.

Experiment 3

The samples listed below were tested for the virus neutralization activity of the anti-RSV IgA antibody in the nasal cavity wash. As an RSV antigen, the RSV-F protein was employed. The animals, immunization method and nasal cavity wash preparation were similar to those in Experiment 2.

Physiological saline

RSV+SF-10 (Example 1)

1. Neutralization Activity Measurement

As the virus neutralization activity of the anti-RSV-F IgA antibody in the nasal cavity wash, the change in the neutralized virus titer was measured by a 50% cytopathogenic endpoint method ($TCID_{50}$ method, Reed L J & Muench H. Am J Hygiene 27: 493-497, 1938). As a rapid and simple measurement of $TCID_{50}$ which was appropriate for the RSV, a combination of a method by Kaul T N at al (Kaul T N, Welliver R C, Ogra P L. J Cin Microbiol 13(5): 957-962, 1981) with an imaging measurement using naphthol blue-black (Perricone M A, Saldate V, Hyde D M. Microsc Res Tech 31(3): 257-264, 1995) was employed and the measurement was conducted as described below. To a 96-well Nunc immunoplate, $2 \times 10^5$ HEp-2 cells were added and cultured overnight. A nasal cavity wash was applied in advance to a KAPTIV-AE™ IgA-affinity column (Tecnogen S.p.A., Piacenza, Italy) to partially purify an IgA fraction (whole IgA) to obtain a sample adjusted to 50 µg/50 µL, to which 50 µL of serially diluted solution (20, 60, 180, 540, 1620, 4820, and 14580-fold dilutions) of a clinically isolated RSV A virus strain (contributed by Sendai virus center) was added to make 100 µL, which was allowed to react for 30 minutes at room temperature and then added to the cells. After culturing the cells at 37° C. for 72 hours, the cells were fixed using a 10% formalin for 10 minutes and then a naphthol blue-black was used to stain the cells for 30 minutes. The degenerated cells were removed by washing twice with a running water, and the cells remaining on the plate were dissolved in 100 µL of 0.1 N NaOH and subjected to the measurement of the absorbance at 630 nm to determine the cytopathogenic endpoint.

2. Results

The $TCID_{50}$ titer of the virus observed was $1 \times 10^{3.7}$ under the conditions involving addition of the IgA fraction collected from a mouse treated nasally with a physiological saline to the cell culture system, while the $TCID_{50}$ titer fell to $1 \times 10^{2.7}$ by the IgA fraction derived from the RSV+SF-10 (Example 1), showing a reduction in the virus titer to a 1/10 level. Although the data are not shown, almost similar values were obtained when testing Example 2's RSV+SF-10F-derived sample. Based on these results, the inventive composition (mucosal vaccine RSV+SF-10 and RSV+SF-10F)-induced nasal cavity washes were revealed to have an RSV neutralization activity and to exert an infection-preventing effect.

The invention claimed is:

1. A composition comprising:
   (a) an antigen-drug (AD) vehicle consisting of a synthetic peptide and a lipid(s), wherein the synthetic peptide consisting of the amino acid sequence KnLm (wherein n is 4 to 8 and m is 11 to 20);
   (b) a carboxyvinyl polymer; and,
   (c) an F protein of a Respiratory Syncytial Virus (RSV) as an antigen.

2. The composition of claim 1, wherein the composition is a pharmaceutical composition.

3. The composition of claim 1, wherein the composition is a mucosal vaccine.

4. The composition of claim 3, wherein the composition is a mucosal vaccine for a transnasal administration.

5. The composition of claim 1, wherein the synthetic peptide consists of the amino acid sequence of SEQ ID NO: 1 or 2.

6. The composition of claim 1, wherein the lipid is at least one of phosphatidyl choline, dipalmitoylphosphatidyl choline, phosphatidyl serine, phosphatidyl glycerol, phosphatidyl inositol, phosphatidyl ethanolamine, phosphatidic acid, lauric acid, myristic acid, palmitic acid, stearic acid and oleic acid.

7. The composition of claim 6, wherein the lipids are a mixture of dipalmitoylphosphatidyl choline, phosphatidyl glycerol and palmitic acid.

8. The composition of claim 1, which is produced by subjecting a mixture of the RSV-F protein and the AD vehicle to freeze-dry or ultrasonic treatment, and mixing the carboxyvinyl polymer with the mixture.

* * * * *

SEQUENCE LISTING

<160> NUMBER OF SEQ ID NOS: 4

<210> SEQ ID NO 1
<211> LENGTH: 22

```
<212> TYPE: PRT
<213> ORGANISM: artificial
<220> FEATURE:
<223> OTHER INFORMATION: Description of artificial sequence: synthetic
      peptide

<400> SEQUENCE: 1

Lys Lys Lys Lys Lys Lys Leu Leu Leu Leu Leu Leu Leu Leu Leu
1               5                   10                  15

Leu Leu Leu Leu Leu Leu
            20

<210> SEQ ID NO 2
<211> LENGTH: 17
<212> TYPE: PRT
<213> ORGANISM: artificial
<220> FEATURE:
<223> OTHER INFORMATION: Description of artificial sequence: synthetic
      peptide

<400> SEQUENCE: 2

Lys Lys Lys Lys Lys Lys Leu Leu Leu Leu Leu Leu Leu Leu Leu
1               5                   10                  15

Leu

<210> SEQ ID NO 3
<211> LENGTH: 1629
<212> TYPE: DNA
<213> ORGANISM: respiratory syncytial virus
<220> FEATURE:
<221> NAME/KEY: CDS
<222> LOCATION: (1)..(1629)

<400> SEQUENCE: 3
```

| | | | | | | | | | | | | | | | | |
|---|---|---|---|---|---|---|---|---|---|---|---|---|---|---|---|---|
| atg | gag | ctg | ctc | atc | ttg | aag | gct | aac | gcc | att | acc | act | atc | ctt | aca | 48 |
| Met | Glu | Leu | Leu | Ile | Leu | Lys | Ala | Asn | Ala | Ile | Thr | Thr | Ile | Leu | Thr | |
| 1 | | | | 5 | | | | | 10 | | | | | 15 | | |
| gcg | gtg | acg | ttc | tgc | ttt | gca | tcc | ggt | cag | aat | att | acc | gaa | gag | ttc | 96 |
| Ala | Val | Thr | Phe | Cys | Phe | Ala | Ser | Gly | Gln | Asn | Ile | Thr | Glu | Glu | Phe | |
| | | | 20 | | | | | 25 | | | | | 30 | | | |
| tac | caa | tct | act | tgt | agc | gct | gtc | tca | aaa | ggc | tat | ctg | tcg | gcc | ctc | 144 |
| Tyr | Gln | Ser | Thr | Cys | Ser | Ala | Val | Ser | Lys | Gly | Tyr | Leu | Ser | Ala | Leu | |
| | | 35 | | | | | 40 | | | | | 45 | | | | |
| cgt | aca | gga | tgg | tac | acg | agt | gtt | atc | acc | atc | gaa | ttg | tcc | aac | att | 192 |
| Arg | Thr | Gly | Trp | Tyr | Thr | Ser | Val | Ile | Thr | Ile | Glu | Leu | Ser | Asn | Ile | |
| | 50 | | | | | 55 | | | | | 60 | | | | | |
| aag | gag | aac | aag | tgc | aac | ggt | act | gac | gcg | aag | gta | aag | ctt | atc | aaa | 240 |
| Lys | Glu | Asn | Lys | Cys | Asn | Gly | Thr | Asp | Ala | Lys | Val | Lys | Leu | Ile | Lys | |
| 65 | | | | | 70 | | | | | 75 | | | | | 80 | |
| cag | gaa | ctg | gat | aag | tac | aag | aac | gca | gtg | aca | gag | ctc | caa | ttg | ctg | 288 |
| Gln | Glu | Leu | Asp | Lys | Tyr | Lys | Asn | Ala | Val | Thr | Glu | Leu | Gln | Leu | Leu | |
| | | | | 85 | | | | | 90 | | | | | 95 | | |
| atg | cag | tct | acc | ccc | gct | acg | aat | aac | cgc | gct | agg | aga | gaa | ctt | cca | 336 |
| Met | Gln | Ser | Thr | Pro | Ala | Thr | Asn | Asn | Arg | Ala | Arg | Arg | Glu | Leu | Pro | |
| | | | 100 | | | | | 105 | | | | | 110 | | | |
| cga | ttc | atg | aac | tat | act | ctc | aat | aac | gcc | aaa | aag | acc | aac | gtc | aca | 384 |
| Arg | Phe | Met | Asn | Tyr | Thr | Leu | Asn | Asn | Ala | Lys | Lys | Thr | Asn | Val | Thr | |
| | | 115 | | | | | 120 | | | | | 125 | | | | |
| ttg | agc | aaa | aag | cag | aag | caa | cag | gct | att | gcg | tcg | ggc | gta | gcc | gtg | 432 |
| Leu | Ser | Lys | Lys | Gln | Lys | Gln | Gln | Ala | Ile | Ala | Ser | Gly | Val | Ala | Val | |
| | 130 | | | | | 135 | | | | | 140 | | | | | |
| agt | aaa | gtc | ctt | cac | ttg | gag | gga | gaa | gtt | aat | aag | atc | aag | tcc | gca | 480 |
| Ser | Lys | Val | Leu | His | Leu | Glu | Gly | Glu | Val | Asn | Lys | Ile | Lys | Ser | Ala | |

```
                        145                 150                 155                 160
ctc ctg tct act aac aaa gct gtg gtc agc ttg tca aac ggt gta tcc        528
Leu Leu Ser Thr Asn Lys Ala Val Val Ser Leu Ser Asn Gly Val Ser
                165                 170                 175 gtg ctg acc tcg aag gtt ctt gac ctc aaa aat tac atc gat aag caa        576
Val Leu Thr Ser Lys Val Leu Asp Leu Lys Asn Tyr Ile Asp Lys Gln
            180                 185                 190 ttg ctg ccg att gtc aac aag cag agt tgt tct atc agc aat att gag        624
Leu Leu Pro Ile Val Asn Lys Gln Ser Cys Ser Ile Ser Asn Ile Glu
        195                 200                 205 acg gtg atc gag ttc caa cag aaa aac aac aga ctc ctg gaa atc aca        672
Thr Val Ile Glu Phe Gln Gln Lys Asn Asn Arg Leu Leu Glu Ile Thr
    210                 215                 220 cgt gag ttt tca gta aat gcc ggc gtt act acc ccc gtc tcc acg tac        720
Arg Glu Phe Ser Val Asn Ala Gly Val Thr Thr Pro Val Ser Thr Tyr
225                 230                 235                 240 atg ctt aca aac tcg gaa ttg ctc agt ctg att aac gac atg cct atc        768
Met Leu Thr Asn Ser Glu Leu Leu Ser Leu Ile Asn Asp Met Pro Ile
                245                 250                 255 act aat gat cag aag aag ctt atg tct aac aac gtg caa att gtc cgc        816
Thr Asn Asp Gln Lys Lys Leu Met Ser Asn Asn Val Gln Ile Val Arg
            260                 265                 270 cag caa agc tat tcc atc atg tca atc att aaa gag gaa gtg ttg gcg        864
Gln Gln Ser Tyr Ser Ile Met Ser Ile Ile Lys Glu Glu Val Leu Ala
        275                 280                 285 tac gta gtt cag ctc cca ctg tac gga gtc atc gac acc ccg tgc tgg        912
Tyr Val Val Gln Leu Pro Leu Tyr Gly Val Ile Asp Thr Pro Cys Trp
    290                 295                 300 aag ctt cat acc tcg ccc ttg tgt acg aca aat act aaa gag ggt tct        960
Lys Leu His Thr Ser Pro Leu Cys Thr Thr Asn Thr Lys Glu Gly Ser
305                 310                 315                 320 aac att tgc ctc acc agg acg gat cga ggc tgg tat tgc gat aac gct       1008
Asn Ile Cys Leu Thr Arg Thr Asp Arg Gly Trp Tyr Cys Asp Asn Ala
                325                 330                 335 gga agt gtg agc ttc ttc cct caa gca gaa aca tgt aag gta cag tcc       1056
Gly Ser Val Ser Phe Phe Pro Gln Ala Glu Thr Cys Lys Val Gln Ser
            340                 345                 350 aat aga gtt ttt tgc gac act atg aac tca ctg acc ctt cca tct gag       1104
Asn Arg Val Phe Cys Asp Thr Met Asn Ser Leu Thr Leu Pro Ser Glu
        355                 360                 365 gtc aat ttg tgt aac gtc gat atc ttc aac ccg aag tac gac tgc aaa       1152
Val Asn Leu Cys Asn Val Asp Ile Phe Asn Pro Lys Tyr Asp Cys Lys
    370                 375                 380 att atg acg tcc aag aca gat gtg tcg agt agc gta atc act tca ctc       1200
Ile Met Thr Ser Lys Thr Asp Val Ser Ser Ser Val Ile Thr Ser Leu
385                 390                 395                 400 ggt gcc atc gtt tct tgc tac ggc aag acc aaa tgt acg gct tcc aat       1248
Gly Ala Ile Val Ser Cys Tyr Gly Lys Thr Lys Cys Thr Ala Ser Asn
                405                 410                 415 aag aac cgt gga att atc aaa aca ttc tcg aac ggt tgc gac tat gtc       1296
Lys Asn Arg Gly Ile Ile Lys Thr Phe Ser Asn Gly Cys Asp Tyr Val
            420                 425                 430 agc aat aag ggc gtg gac act gtg agt gta gga aac acc ctg tac tac       1344
Ser Asn Lys Gly Val Asp Thr Val Ser Val Gly Asn Thr Leu Tyr Tyr
        435                 440                 445 gtt aac aag caa gaa ggt aaa tca ctg tat gtc aag ggc gag ccc att       1392
Val Asn Lys Gln Glu Gly Lys Ser Leu Tyr Val Lys Gly Glu Pro Ile
    450                 455                 460 atc aat ttt tac gat cct ctt gtg ttc cca tcc gac gag ttc gat gcg       1440
```

```
Ile Asn Phe Tyr Asp Pro Leu Val Phe Pro Ser Asp Glu Phe Asp Ala
465                 470                 475                 480 tct atc agc cag gta aac gaa aag att aac cag tcc ttg gca ttt atc     1488
Ser Ile Ser Gln Val Asn Glu Lys Ile Asn Gln Ser Leu Ala Phe Ile
                    485                 490                 495 cgc aaa tcg gac gag ctc ctg cac aat gtt aac gcc gga aag agt acg     1536
Arg Lys Ser Asp Glu Leu Leu His Asn Val Asn Ala Gly Lys Ser Thr
                500                 505                 510 aca aac att atg tct aga ctg gtt ccg cgt gga tcc ggc tct gga tct     1584
Thr Asn Ile Met Ser Arg Leu Val Pro Arg Gly Ser Gly Ser Gly Ser
            515                 520                 525 ggc ctc agg atg ggg ggt tct gac tac aag gac gat gac gac aag         1629
Gly Leu Arg Met Gly Gly Ser Asp Tyr Lys Asp Asp Asp Asp Lys
        530                 535                 540
```

<210> SEQ ID NO 4
<211> LENGTH: 543
<212> TYPE: PRT
<213> ORGANISM: respiratory syncytial virus

<400> SEQUENCE: 4

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
            115                 120                 125

Leu Ser Lys Lys Gln Lys Gln Gln Ala Ile Ala Ser Gly Val Ala Val
130                 135                 140

Ser Lys Val Leu His Leu Glu Gly Glu Val Asn Lys Ile Lys Ser Ala
145                 150                 155                 160

Leu Leu Ser Thr Asn Lys Ala Val Val Ser Leu Ser Asn Gly Val Ser
                165                 170                 175

Val Leu Thr Ser Lys Val Leu Asp Leu Lys Asn Tyr Ile Asp Lys Gln
                180                 185                 190

Leu Leu Pro Ile Val Asn Lys Gln Ser Cys Ser Ile Ser Asn Ile Glu
            195                 200                 205

Thr Val Ile Glu Phe Gln Gln Lys Asn Asn Arg Leu Leu Glu Ile Thr
210                 215                 220

Arg Glu Phe Ser Val Asn Ala Gly Val Thr Thr Pro Val Ser Thr Tyr
225                 230                 235                 240

Met Leu Thr Asn Ser Glu Leu Leu Ser Leu Ile Asn Asp Met Pro Ile
                245                 250                 255

Thr Asn Asp Gln Lys Lys Leu Met Ser Asn Asn Val Gln Ile Val Arg
            260                 265                 270

Gln Gln Ser Tyr Ser Ile Met Ser Ile Ile Lys Glu Glu Val Leu Ala
```

|     |     |     |     |     | 275 |     |     |     | 280 |     |     |     |     | 285 |     |     |
| --- | --- | --- | --- | --- | --- | --- | --- | --- | --- | --- | --- | --- | --- | --- | --- | --- |
| Tyr | Val | Val | Gln | Leu | Pro | Leu | Tyr | Gly | Val | Ile | Asp | Thr | Pro | Cys | Trp |
|     |     |     | 290 |     |     |     | 295 |     |     |     | 300 |     |     |     |     |
| Lys | Leu | His | Thr | Ser | Pro | Leu | Cys | Thr | Thr | Asn | Thr | Lys | Glu | Gly | Ser |
| 305 |     |     |     |     | 310 |     |     |     |     | 315 |     |     |     |     | 320 |
| Asn | Ile | Cys | Leu | Thr | Arg | Thr | Asp | Arg | Gly | Trp | Tyr | Cys | Asp | Asn | Ala |
|     |     |     |     | 325 |     |     |     |     | 330 |     |     |     |     | 335 |     |
| Gly | Ser | Val | Ser | Phe | Phe | Pro | Gln | Ala | Glu | Thr | Cys | Lys | Val | Gln | Ser |
|     |     |     | 340 |     |     |     |     | 345 |     |     |     |     | 350 |     |     |
| Asn | Arg | Val | Phe | Cys | Asp | Thr | Met | Asn | Ser | Leu | Thr | Leu | Pro | Ser | Glu |
|     |     | 355 |     |     |     |     | 360 |     |     |     |     | 365 |     |     |     |
| Val | Asn | Leu | Cys | Asn | Val | Asp | Ile | Phe | Asn | Pro | Lys | Tyr | Asp | Cys | Lys |
|     | 370 |     |     |     |     | 375 |     |     |     |     | 380 |     |     |     |     |
| Ile | Met | Thr | Ser | Lys | Thr | Asp | Val | Ser | Ser | Ser | Val | Ile | Thr | Ser | Leu |
| 385 |     |     |     |     |     | 390 |     |     |     |     | 395 |     |     |     | 400 |
| Gly | Ala | Ile | Val | Ser | Cys | Tyr | Gly | Lys | Thr | Lys | Cys | Thr | Ala | Ser | Asn |
|     |     |     |     | 405 |     |     |     |     | 410 |     |     |     |     | 415 |     |
| Lys | Asn | Arg | Gly | Ile | Ile | Lys | Thr | Phe | Ser | Asn | Gly | Cys | Asp | Tyr | Val |
|     |     |     | 420 |     |     |     |     | 425 |     |     |     |     | 430 |     |     |
| Ser | Asn | Lys | Gly | Val | Asp | Thr | Val | Ser | Val | Gly | Asn | Thr | Leu | Tyr | Tyr |
|     |     | 435 |     |     |     |     | 440 |     |     |     |     | 445 |     |     |     |
| Val | Asn | Lys | Gln | Glu | Gly | Lys | Ser | Leu | Tyr | Val | Lys | Gly | Glu | Pro | Ile |
|     | 450 |     |     |     |     | 455 |     |     |     |     | 460 |     |     |     |     |
| Ile | Asn | Phe | Tyr | Asp | Pro | Leu | Val | Phe | Pro | Ser | Asp | Glu | Phe | Asp | Ala |
| 465 |     |     |     |     | 470 |     |     |     |     | 475 |     |     |     |     | 480 |
| Ser | Ile | Ser | Gln | Val | Asn | Glu | Lys | Ile | Asn | Gln | Ser | Leu | Ala | Phe | Ile |
|     |     |     |     | 485 |     |     |     |     | 490 |     |     |     |     | 495 |     |
| Arg | Lys | Ser | Asp | Glu | Leu | Leu | His | Asn | Val | Asn | Ala | Gly | Lys | Ser | Thr |
|     |     |     | 500 |     |     |     |     | 505 |     |     |     |     | 510 |     |     |
| Thr | Asn | Ile | Met | Ser | Arg | Leu | Val | Pro | Arg | Gly | Ser | Gly | Ser | Gly | Ser |
|     |     | 515 |     |     |     |     | 520 |     |     |     |     | 525 |     |     |     |
| Gly | Leu | Arg | Met | Gly | Gly | Ser | Asp | Tyr | Lys | Asp | Asp | Asp | Lys |     |     |
|     | 530 |     |     |     |     | 535 |     |     |     |     | 540 |     |     |     |     |